United States Patent
Wei

(10) Patent No.: US 7,631,970 B2
(45) Date of Patent: Dec. 15, 2009

(54) OPTICAL APPARATUS AND METHODS FOR PERFORMING EYE EXAMINATIONS

(75) Inventor: Jay Wei, Fremont, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 268 days.

(21) Appl. No.: 11/056,537

(22) Filed: Feb. 10, 2005

(65) Prior Publication Data

US 2005/0203422 A1 Sep. 15, 2005

Related U.S. Application Data

(60) Provisional application No. 60/543,862, filed on Feb. 10, 2004.

(51) Int. Cl.
*A61B 3/10* (2006.01)
*A61B 3/00* (2006.01)

(52) U.S. Cl. .................. 351/211; 351/246; 351/205

(58) Field of Classification Search ................ 351/246, 351/243, 211–212
See application file for complete search history.

(56) References Cited

U.S. PATENT DOCUMENTS

| | | | |
|---|---|---|---|
| 1,377,740 A * | 5/1921 | Uribe-Troncoso | 434/271 |
| 3,767,307 A | 10/1973 | Bowker | |
| 5,202,745 A | 4/1993 | Sorin et al. | |
| 5,321,501 A | 6/1994 | Swanson et al. | |
| 5,371,588 A | 12/1994 | Davis et al. | |
| 5,520,679 A * | 5/1996 | Lin | 606/5 |
| 5,537,162 A * | 7/1996 | Hellmuth et al. | 351/206 |
| 5,894,531 A | 4/1999 | Alcoz | |
| 6,053,613 A * | 4/2000 | Wei et al. | 351/205 |
| 6,252,666 B1 | 6/2001 | Mandella et al. | |
| 6,325,512 B1 * | 12/2001 | Wei | 351/209 |
| 6,385,358 B1 | 5/2002 | Everett et al. | |
| 6,501,551 B1 | 12/2002 | Teamey et al. | |
| 6,575,573 B2 | 6/2003 | Lal et al. | |
| 6,822,741 B2 | 11/2004 | Aronkyto et al. | |
| 7,046,371 B2 | 5/2006 | De Lega et al. | |

(Continued)

FOREIGN PATENT DOCUMENTS

DE 198 57 001 A1 6/2000

(Continued)

OTHER PUBLICATIONS

Gregor F. Schmid, Axial and peripheral eye length measured with optical low coherance reflectometry, Journal of Biomedical Optics 8(4), 655-662 Oct. 2003.*

(Continued)

*Primary Examiner*—Ricky L Mack
*Assistant Examiner*—James R Greece
(74) *Attorney, Agent, or Firm*—Haynes & Boone LLP

(57) ABSTRACT

An eye examination system is presented that obtains several parameters of the eye. A system according to some embodiments of the present invention include a keratometry system, a low coherence reflectometry system, and a low coherence interferometry system co-coupled to the eye. In some embodiments, the low coherence interferometry system can provide interferometric tomography data. A processor can be coupled to receive data from the keratometry system, the low coherence reflectometry system, and the low coherence interferometry system and calculate at least one parameter of the eye from that data.

1 Claim, 4 Drawing Sheets

U.S. PATENT DOCUMENTS

| | | | |
|---|---|---|---|
| 7,102,756 | B2 | 9/2006 | Izatt et al. |
| 7,280,221 | B2 | 10/2007 | Wei |
| 2003/0011745 | A1* | 1/2003 | Molebny et al. ............ 351/215 |
| 2003/0028100 | A1 | 2/2003 | Tearney et al. |
| 2005/0140982 | A1 | 6/2005 | Chen et al. |
| 2005/0174578 | A1 | 8/2005 | Wei |
| 2006/0058682 | A1* | 3/2006 | Miller et al. ................ 600/476 |

FOREIGN PATENT DOCUMENTS

| | | |
|---|---|---|
| EP | 0 697 611 A2 | 2/1996 |
| WO | WO 00/28884 | 5/2000 |
| WO | WO 03/105678 A2 | 12/2003 |

OTHER PUBLICATIONS

International Search Report and Written Opinion from related PCT Application No. PCT/US2005/003871 filed Feb. 9, 2005.

Izatt, J. et al., "Micrometer-Scale Resolution Imaging of the Anterior Eye in Vivo With Optical Coherence Tomography," Arch Ophthalmol (1994), vol. 112, pp. 1584-1589.

U.S. Appl. No. 11/055,900, filed Feb. 10, 2005.

Danielson, B.L. et al., "Guided-Wave Reflectometry with Micrometer Resolution," Applied Optics (1987), vol. 26, No. 14, pp. 2836-2842.

Golubovic, B. et al., "Optical Frequency-Domain Reflectometry Using Rapid Wavelength Tuning of a $Cr^{4+}$:Forsterite Laser," Optical Society of America (1997), vol. 22, No. 22, pp. 1704-1706.

Halgis, W. et al., "Comparison of Immersion Ultrasound Biometry and Partial Coherence Interferometry for Introcular Lens Calculation According to Haigis," Graefe's Arch Clin Exp Ophthalmol (2000) 238: 765-773.

Hamed et al., "A Comparative Analysis of Five Methods of Determining Corneal Refractive Power in Eyes that have Undergone Myopic Laser in Situ Keratomileusis," American Academy of Ophthalmology (2000), vol. 109, No. 4, pp. 651-658.

Hee, M. et al., "Polarization-Sensitive Low-Coherence Reflectometer for Birefringence Characterization and Ranging," Opitcal Society of America (1992), vol. 9, No. 6, pp. 903-908.

Hitzenberger, C.K et al., "Measurement of the Axial Eye Length and Retinal Thickness by Laser Doppler Interferometry (LDI)," Ophthalmic Technologies (1991), vol. 1423. pp. 46-50.

Huang, D. et al., "Opitcal Coherence Tomography," Science (1991), vol. 254, pp. 1178-1181.

Kobayashi, M. et al., "Polarization-Independent Interferometric Optical-Time-Domain Reflectometer," IEEE (1991), vol. 9, No. 5, 6 pages.

Park, H. et al., "High Resolution Optical Ranging System," Applied Optics (1981), vol. 20. No. 14, pp. 2389-2394.

Preussner, P.R., "Ray Tracing for Intraocular Lens Calculation," Elsvier Science Inc. (2001), vol. 28, pp. 1412-1419.

Radhakrishnam, S. et al., "Real-Time Optical Coherence Tomography of the Anterior Segment at 1310 nm," American Medical Association (2001), vol. 119, pp. 1179-1185.

Rollins, A. et al., "Optimal Interferometer Designs for Optical Coherence Tomography," Optical Society of America (1999), vol. 24, No. 21, pp. 1-3.

Sorin, W.V. et al., "Simultaneous Thickness and Group index Measurement Using Opitcal Low-Coherence Reflectometry," IEEE (1992), vol. 4, No. 1, pp. 105-107.

Takada, K. et al., "New Measurement System for Fault Location in Optical Waveguide Devices Baded on an Interferometric Technique," Applied Optics (1987), vol. 26, vol. 9, pp. 1603-1606.

Andrew M. Rollins and Joseph A. Izatt, "Optimal Interferometer Designs for Optical Coherence Tomography," Optics Letters, vol. 24, No. 21, Nov. 1, 1999, pp. 1484-1486.

Michael R. Hee and David Huang, Eric A. Swanson, James G. Fujimoto, "Polarization-Sensitive Low-Coherence Reflectometer for Birefringence Characterization and Ranging," Journal of the Optical Society of America B, vol. 9, No. 6, Jun. 1992, pp. 903-908.

Non-final Office Action dated Feb. 16, 2007, in U.S. Appl. No. 11/055,900.

Amendment and Response to Office Action filed May 3, 2007, in U.S. Appl. No. 11/055,900.

Notice of Allowance dated Jun. 1, 2007, in U.S. Appl. No. 11/055,900.

\* cited by examiner

OPTICAL APPARATUS AND METHODS FOR PERFORMING EYE EXAMINATIONS

RELATED APPLICATIONS

The present application claims priority to Provisional Application No. 60/543,862, "Optical Apparatus and Methods for Eye Examine," by Jay Wei, filed on Feb. 10, 2004, which is herein incorporated by reference in its entirety.

BACKGROUND

1. Field of the Invention

The present invention is related to optical apparatus and methods for obtaining parameters in an eye examination and, in particular, to optical interferometric apparatus for performing eye examinations.

2. Discussion of Related Art

Refractive surgery to correct refraction error in the human eye has been widely accepted. Several different types of surgical methods have been explored for this purpose. PRK and LASIK are surgical methods that use laser radiation to ablate cornea tissue in order to change the refractive power of the cornea. Phakic IOL surgery implants intra-ocular lenses in either the anterior or posterior chamber of the eye to compensate for refraction error in the eye. To achieve good clinical outcomes from any of these surgeries, physical dimensions of the eye such as cornea thickness, anterior chamber depth, angle-to-angle width, and sucus-to-sucus width, for example, need to be accurately measured pre-operatively. In some cases, post surgery diagnosis, which is important for patient follow up, also requires good measurements of these physical parameters of the eye.

In another common surgery on the eye, cataract surgery has been performed for many years on cataract patients. To achieve an accurate refraction power as a result of the surgery, parameters of the eye such as the axial length, cornea power, anterior chamber depth, and the equatorial plane of the crystalline lens should be accurately measured in order to calculate the power of the intra-ocular lens to be implanted in a Phakic IOL surgery. The true cornea power is especially important when the cataract surgery is performed on a post-Lasik patient.

There are various existing devices that can be used to measure one or two of these parameters, but not all of them in a single apparatus. To acquire all required parameters for surgical preparation, the measurement of various physical parameters of the eye needs to be performed by different instruments. Sometimes, inconsistency in measured results will occur due to discrepancies between the instruments and discrepancies of alignment of the eye with the various instruments. For example, the cornea power can be measured with an Orbscan (by Orbtek, Bausch & Lomb, Rochester, N.Y.) by combination of Pacido ring and slit projection methods. The Pacido ring method uses multiple concentric ring-shaped light sources to illuminate the eye. The cornea is like a mirror and reflects the illumination from the light sources into a CCD camera. The image size and shape of the rings formed by the cornea can then be used to analyze the contour of the cornea. The slit projection method illuminates the cornea with a thin slit of light. The scattering caused by the illuminated cornea tissue can then be imaged in a CCD camera. The cornea thickness and curvature can be calculated from the image of the illuminated cornea.

Due to the slow scan speed, eye motion effects can cause the results of such a test to be highly inaccurate. The anterior chamber depth can be measured either by the slit projection method (IOL Master (by Carl Zeiss, Jena, Germany), Orbscan (by Orbtek, Bausch & Lomb, Rochester, N.Y.), Ultrasound Microscope (UBM by Paradiam Medical, Salt Lake City, Utah), Artemis (by Ultralink, LLC, St. Petersburg, Fla.), B-scan (by Ophthalmic Technologies, Inc., Toronto, Canada), or Optical Coherence Tomography (OCT) (Case Western Reserve University and Cleveland Clinic Foundation). None of these devices is capable of measuring all required parameters in a single compact apparatus.

Because the refractive surgery and cataract surgery can be performed by the same surgeon, it is desired to have a single compact apparatus to measure all of the parameters required by both refractive and cataract surgeries. Therefore, there is a need to provide a single instrument that provides measurements of groups of parameters in order to eliminate inaccuracies due to utilization of several instruments for measurements of these parameters.

SUMMARY

The current invention is related to an optical apparatus and method for examining an eye in order to obtain a plurality of optical parameters relevant to an optical surgery on the eye. The optical apparatus is associated with a low coherence interferometer that can be used for non-invasive optical imaging and measurement.

An eye examination system according to the present invention can include a low coherence reflectometer coupled to illuminate an eye; a low coherence interferometer coupled to illuminate the eye; an LED and camera system coupled to measure a virtual image of the LEDs reflected from the eye; and a processor coupled to receive data from the low coherence reflectometer, the low coherence interferometer, and the camera system and to calculate at least one parameter of the eye. In some embodiments, the system can further include a visual target coupled to provide an image to the eye.

A method of obtaining eye parameters according to the present invention can include receiving reflectometry data from a low coherence reflectometer coupled to an eye; receiving interferometry data from a low coherence interferometer coupled to the eye; receiving keratometry data from a camera coupled to receive a virtual image of a plurality of LEDs from the eye; and calculating at least one parameter of the eye.

These and other embodiments are further discussed below with respect to the following figures.

In the figures, elements having the same designation have the same or similar functions.

DETAILED DESCRIPTION

Figure 1A:
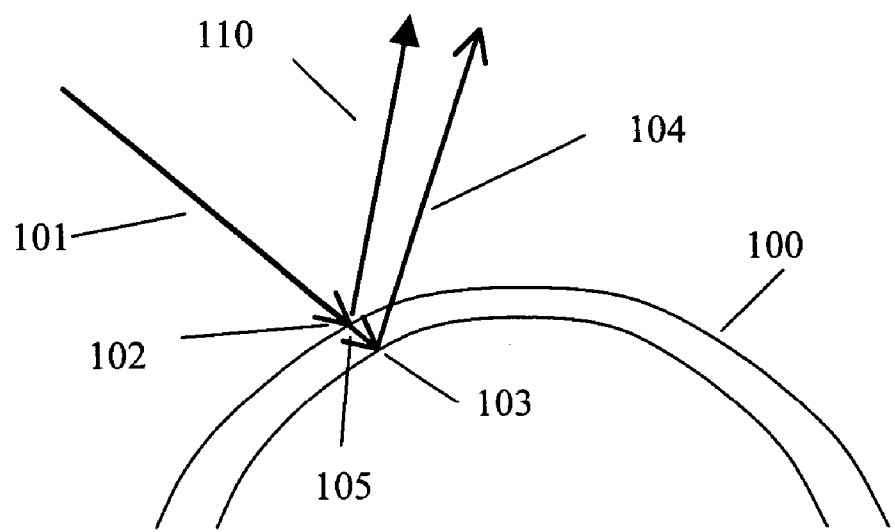
FIGS. 1A and 1B illustrate measurements of the cornea power and cornea thickness of an eye.
Figure 1B:
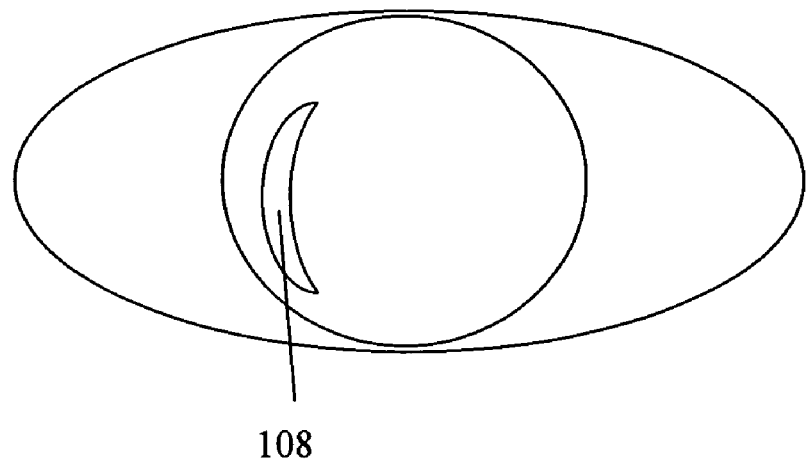

FIGS. 1A and 1B illustrate a current state-of-the-art slit projection method to measure cornea thickness. As shown in FIG. 1A, a slit of light 101, also referred to herein as a slit beam, is projected on to a cornea 100. Light 110 is reflected from a front surface 102 of cornea 100 and light 104 is reflected from a back surface 103 of cornea 100. Also, because the cornea will scatter light, the segment of cornea stoma 105 will be seen by an observer or CCD camera through an imaging system. A corresponding reflection image 108 from eye 111 of slit beam 101 that is scanned across cornea 100 has a shape of an early moon on the cornea. From an incident angle of slit beam 101 and imaging system parameters, the thickness of cornea 100 can be calculated from the width of a moon-like reflection image 108. In principle, the cornea curvature can also be calculated from reflected light 110 and 104. But limited by the scan speed of the slit beam 101 (in the 1 to 2 seconds range), eye motion can cause the measurement to be inaccurate. As a result, cornea power has not been measured by the slit projection principle alone. Orbscan (by B&L) add a Placido ring illumination system to map the front surface cornea curvature and use the thickness to estimate the back cornea surface curvature. The cornea power can then be calculated from these data associated with index of refraction of cornea tissue, which is essentially a constant. The accuracy of this approach suffers due to the inaccuracy of cornea thickness measurement.

Figure 2:
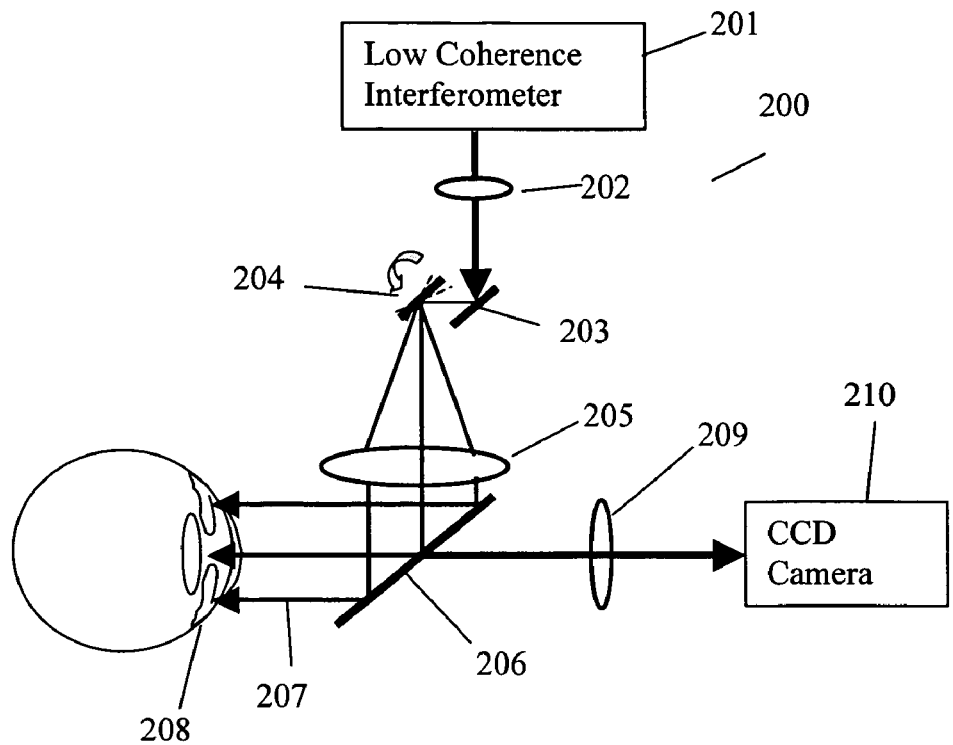
FIG. 2 illustrates a system for conventionally measuring the Sim-K, anterior chamber depth, and the eye axial length.

FIG. 2 illustrates an examination system 200 for performing optical coherence tomography (OCT) on an eye 208. Optical coherence tomography (OCT) presents a better method of measuring the cornea thickness due to its superior optical resolution. Cornea imaging by OCT with a 10 to 20 µm optical resolution has been demonstrated by Cleveland Clinic Foundation (Arch. of Ophtal. Vol. 119, No. 8, 1179-1185, August 2001). The accuracy is a couple of orders of magnitude better than the slit projection method discussed above with respect to FIG. 1.

The measurement system shown in FIG. 2 illustrates a common optical examination system 200 for a cornea scan OCT system. The light from a low coherence interferometer 201 is collimated by a lens 202. Mirrors 203 and 204 can be mounted relative to each other to intercept and direct an optical beam from collimating lens 202. Mirrors 203 and 204 can be driven by a scanning mechanism that can scan the beam in two dimensions. A scanning lens 205 can be positioned to intercept the beam from mirror 204 and focus a beam 207 onto the anterior chamber of eye 208. Scanning mirrors 203 and 204 can be located proximately to the back focal plane of lens 205 so that scanning beam 207 is parallel. A beamsplitter 206 can be positioned to receive beam 207 from lens 205. Beamsplitter 206 is a dichroic beamsplitter that reflects beam 207 into eye 208 but transmits a video image from eye 208, illuminated with different wavelengths other than the wavelength of the light source in interferometer 201, to a CCD camera system 210. Enough light is reflected back into interferometer 201 by beam splitter 206 for interferometer 201 to operate appropriately. In some embodiments, an imaging lens 209 can be placed between beamsplitter 206 and CCD camera system 210. Again, due to scan time (current state of art is about 125 ms for one single scan), the desired accuracy of a calculated cornea curvature parameter based on examination system 200 is still not feasible with the OCT scan method because of the inability to immobilize eye 208 during the test.

Lenses and other optical systems shown in this disclosure (e.g., lenses 205 and 209) can include any number of optical components to accomplish the described function. The lenses and other optical components illustrated here are utilized to demonstrate the overall function.

Figure 3:
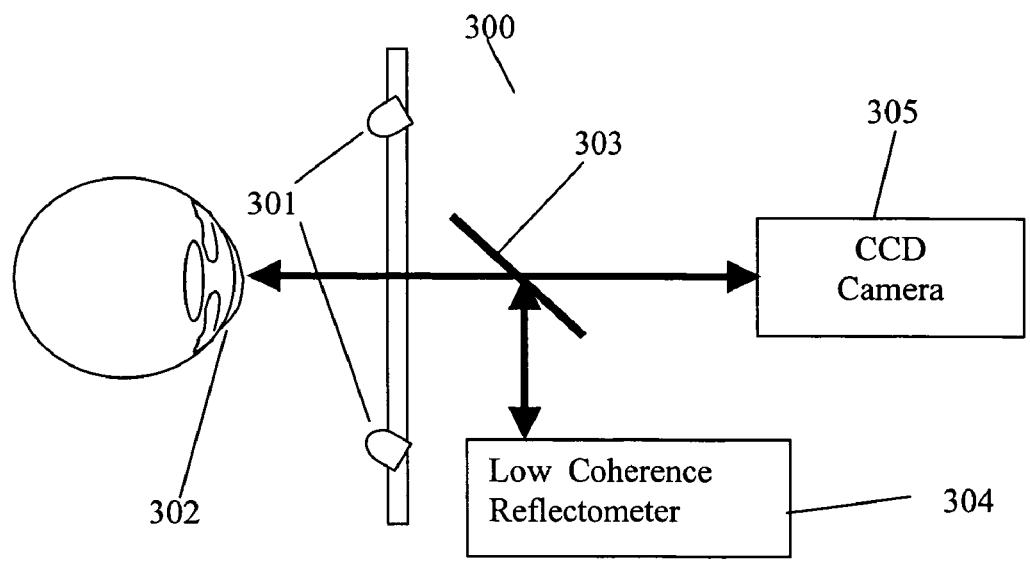
FIG. 3 illustrates a system for conventionally measuring the angle-to-angle width, anterior chamber depth, and cornea thickness of an eye.

FIG. 3 illustrates another conventional examination system 300 that provides a combination of three different methods to measure parameters required for calculating the power of the intra-ocular lens for cataract surgery. System 300 is commercially available from Carl Zeiss Meditec, Germany. The front surface cornea power is measured with a Keratometer. The anterior chamber depth is measured by a projection slit of light. The axial length of the eye is measured by low coherence reflectometry.

As shown in FIG. 3, the Keratometer is configured with three or more LEDs 301 to illuminate a cornea 302. Light from LEDs 301 is reflected from cornea 302 into a CCD camera 305. Therefore, the virtual image of the LEDs is measured in CCD camera system 305. The cornea curvature structure can be calculated from the virtual image size of the LEDs reflected from a front surface of cornea 302.

A low coherence light source from the sample arm of a low coherence reflectometer 304 is directed into cornea 302 by a beamsplitter 303. A single eye axial length (from cornea to retina) measurement can be performed. In some embodiments, reflectometer 304 can be an OCT interferometer without transverse scan.

The slit projection light source is not shown in system 300 of FIG. 3, but the slit image is imaged on CCD camera 305 for analysis. The true cornea power can not be calculated, because the back cornea surface curvature and cornea thickness are not available utilizing system 300.

Figure 4:
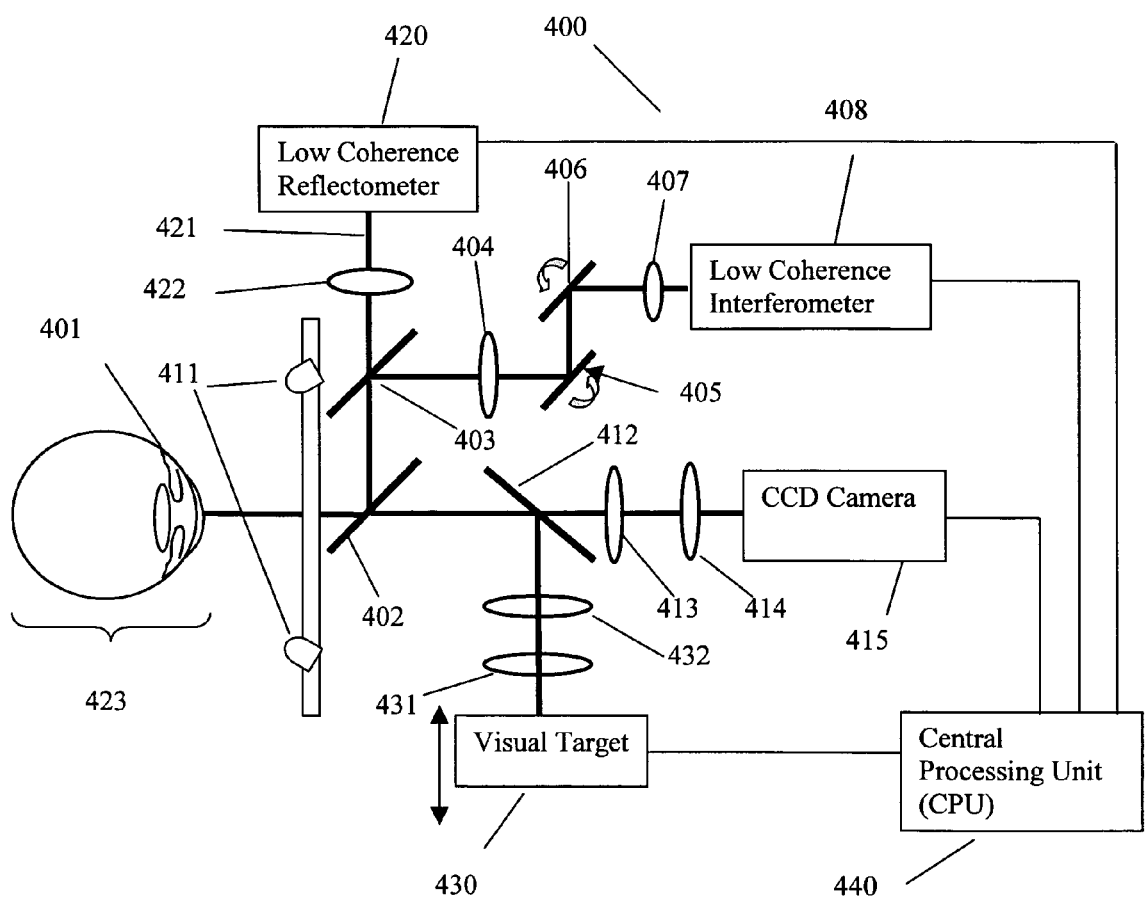
FIG. 4 illustrates an eye measurement system according to some embodiments of the present invention.

FIG. 4 shows an examination system 400 according to some embodiments of the current invention. Some embodiments of system 400 are capable of measuring most, if not all, of the important parameters that are needed in the performance of refractive and cataract surgeries. The anterior chamber eye image is acquired by scanning a near infrared beam on the anterior chamber of an eye 401. A sample beam from a low coherence interferometer 408 is collimated by a lens 407 and spatially scanned by scanning mirrors 406 and 405. Scanning mirrors 406 and 405 can be driven by motors (not shown) in order to scan the beam from interferometer 408 across eye 401. The beam from scanning mirrors 406 and 405 is focused onto the anterior chamber of eye 401 by a scanning lens 404. In some embodiments, beamsplitters 403 and 402 are positioned to direct light between lens 404 and eye 401. Scanning mirrors 406 and 405 are proximately located at the back focal plane of lens 404 in order that the scanning beam from low coherence interferometer 408 is parallel in front of eye 401. The light reflected from the tissue of the anterior chamber of eye 401 will be propagated back into low coherence interferometer 408. The interference signal from low coherence interferometer 408 then will be processed by a central processing unit 440 to form an optical coherence tomography. Low coherence interferometer 408 and a low coherence reflectometer 420 can be one of a number of low coherence interferometer arrangements, including the low coherence interferometers described in U.S. application Ser. No. 11/055,900, filed concurrently with the present application by Jay Wei, herein incorporated by reference in its entirety.

In some embodiments, light from three or more LEDs 411 is reflected from the cornea of eye 401 onto a CCD or CMOS camera 415 in order to measure front surface cornea power. The virtual image of LEDs 411 reflected from the cornea of eye 401 can, in some embodiments, be imaged by lenses 413 and 414 camera 415. The LED image reflected by the cornea of eye 401 onto camera 415 can be acquired in central processing unit 440 for calculating the front surface cornea curvature.

Once the curvature of the front surface cornea is known, the shape of the back surface of the cornea can be obtained by adding the thickness of the cornea, acquired by the optical coherence tomography of the cornea from low coherence interferometer 408, to the front surface shape. With the known average index of refraction of the human cornea, which is 1.38 at an OCT scan wavelength of about 1300 nm, the cornea power can be calculated with a simple well-known optical equation. Central processing unit 440, then, receives the image from camera 415, tomography data from interferometer 408, and reflectometer data from low coherence reflectometer 420 to determine all of the parameters needed to characterize eye 401.

A light beam 421 from low coherence reflectometer 420 can be utilized to measure an eye axial length 423. As shown in FIG. 4, light beam 421 can be projected onto eye 401 by a lens 422 through beamsplitters 403 and 402. More particularly, light beam 421 can be transmitted through beam splitter 403 and reflected into eye 401 by beamsplitter 402. Optical beams reflected from the cornea and retina of eye 401 will propagate back to low coherence reflectometer 420. The distance between the retina and the cornea can then be calculated by central processing unit 440 from the interference signal generated in low coherence reflectometer 420.

In some embodiments, a visual target 430 can be seen by eye 401 of the patient, through lenses 431 and 432 and beamsplitters 412 and 402. The target can move back and forth in a fashion controlled by central processing unit 440 to compensate for the patient's refraction error. Visual target 430 can serve at least three purposes. First, visual target 430 provides a reference for the patient to fixate on during the examine. Second, visual target 430 can force the patient to focus to the desired accommodation distance. Third, visual target 430 can be a visual acuity target for subjective refraction tests on the patient. The second purpose is important for Phakic IOL implant and Presbyopia implant surgery preparation and post surgery diagnosis. The equatorial plane of the crystalline lens to be inserted by these surgeries can either be visualized on a light pigmented iris eye or estimated by the front and back surface of the crystalline lens. The cornea power, anterior chamber depth, equatorial plane of the crystalline lens, and the eye axial length contain all the optical information required by a cataract surgeon to calculate the IOL power for the implant. The angle-to-angle width measured by low coherence interferometer 408 is used for fitting angle supported anterior chamber Phakic IOL, and the sucus-to-sucus width is used for fitting a posterior chamber Phakic IOL.

As shown in FIG. 4, each of LEDs 411, low coherence reflectometer 420, low coherence interferometer 408, and visual target 430 operate at sufficiently different wavelengths that light is routed correctly through system 400. For example, beam splitter 402 reflects light from low coherence reflectometer 420 and low coherence interferometer 408 and passes light from LEDs 411 and from visual target 430. Additionaly, beam splitter 403 transmits light to low coherence reflectometer 420 and reflects light to low coherence interferometer 408. Further, beam splitter 412 transmits light from LEDs 411 and reflects light from visual target 430. In some embodiments of the invention, low coherence reflectometer 420, low coherence interferometer 408, and diodes 411 can be operated simultaneously so that all of the data is taken simultaneously. In some embodiments, however, sequential operation of low coherence reflectometer 420, low coherence interferometer 408, and diodes 411 may be utilized.

Figure 5:
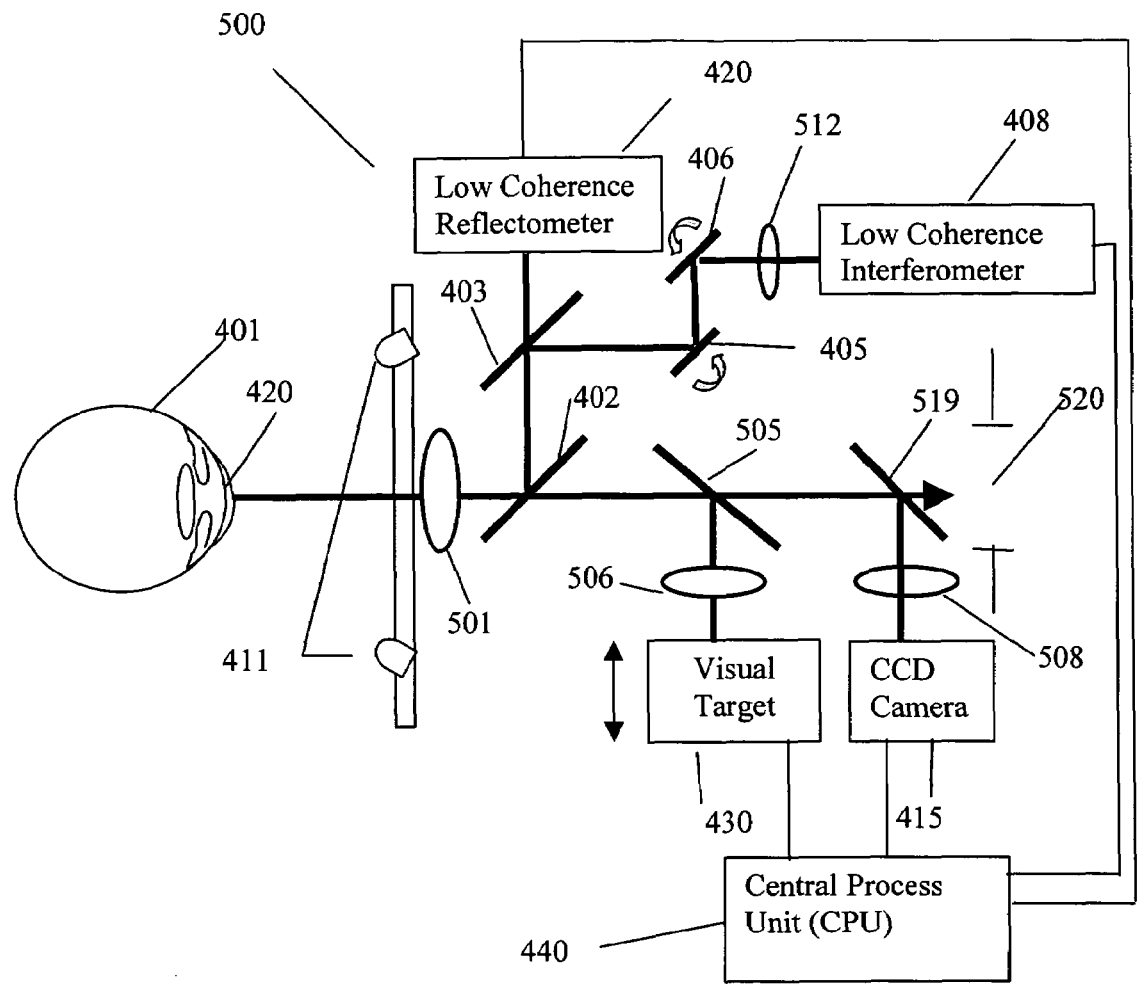
FIG. 5 illustrates another embodiment of an eye measurement system according to some embodiments of the present invention.

FIG. 5 shows an embodiment of measurement system 500, which is another embodiment of the current invention. Because cornea 420 should be positioned at the front focal plane of scanning lens 404, as shown in FIG. 4, and scanning mirrors 405 and 406. should be close to back focal plane of lens 404, beamspitters 402 and 403 increase the total optical path of low coherence interferometer 408. The diameter of imaging lens 432 and 413 also should be increased due to the increase distance between cornea 420 and lens 432. These aspects of system 400 can result in increased size and cost.

In system 500 of FIG. 5, a lens 501 can be placed between eye 401 and beamsplitter 402. It is a common component of all optical paths from eye 401. Such an arrangement significantly reduces the size and cost of system 500 because a lens 512, a lens 506 and a lens 508 can be smaller than lens 407, lenses 432 and 431, and lenses 413 and 414, respectively. Another advantage of system 500 is that a beamsplitter 519 and a window 520 can provide a see-through scene which eliminates the instrument's myopia effect.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An eye examination system, comprising:
   a low coherence reflectometer coupled to a central processing unit and a first beam splitter, the low coherence reflectometer emitting a first light beam which is transmitted through the first beam splitter, a second beam splitter, and a first lens to illuminate an eye;
   a low coherence interferometer coupled to a second lens, first and second scanning mirrors, the first beam splitter, and the central processing unit, the low coherence interferometer emitting a second light beam which is collimated by the second lens, spatially scanned through the first and second scanning mirrors, and transmitted through the first beam splitter, the second beam splitter, and the first lens, to illuminate the eye;
   first and second light emitting diodes (LEDs) coupled to illuminate the eye, wherein light from the first and second LEDs reflected off of the eye is transmitted through the first lens, the second beam splitter, a third beam splitter, a fourth beam splitter, and a third lens to a charge-coupled device (CCD) camera which is coupled to the central processing unit;
   a visual target which is visible to the eye through the third beam splitter, the second beam splitter, and the first lens; and
   a window provided on an optical path of the eye for eliminating a near focus point.

* * * * *